US008906919B2

(12) United States Patent
Smith et al.

(10) Patent No.: US 8,906,919 B2
(45) Date of Patent: Dec. 9, 2014

(54) TREATMENT OF NON-NEURONAL AND NON-MYOCARDIAL CELL, TISSUE AND ORGAN DAMAGE AND ASSOCIATED PAIN WITH PERSISTENT SODIUM CURRENT BLOCKERS

(75) Inventors: Paul Nathaniel Smith, O'Malley (AU); Steven Michael Weiss, Deakin (AU)

(73) Assignee: Ozteo Pty Ltd, O'Malley (AU)

(*) Notice: Subject to any disclaimer, the term of this patent is extended or adjusted under 35 U.S.C. 154(b) by 409 days.

(21) Appl. No.: 13/382,556

(22) PCT Filed: Jun. 29, 2010

(86) PCT No.: PCT/AU2010/000814
§ 371 (c)(1),
(2), (4) Date: Mar. 8, 2012

(87) PCT Pub. No.: WO2011/003129
PCT Pub. Date: Jan. 13, 2011

(65) Prior Publication Data
US 2012/0172363 A1  Jul. 5, 2012

(30) Foreign Application Priority Data
Jul. 9, 2009 (AU) ................................ 2009903235

(51) Int. Cl.
A61K 31/53    (2006.01)
A61K 31/428   (2006.01)
A61K 31/16    (2006.01)
A61K 31/167   (2006.01)

(52) U.S. Cl.
CPC .............. *A61K 31/167* (2013.01); *A61K 31/16* (2013.01); *A61K 31/428* (2013.01); *A61K 31/53* (2013.01)
USPC ............................ 514/242; 514/367; 514/626

(58) Field of Classification Search
CPC ...... A61K 31/53; A61K 31/428; A61K 31/16
USPC ........................................ 514/242, 367, 626
See application file for complete search history.

(56) References Cited

U.S. PATENT DOCUMENTS

| 5,506,229 | A   |   | 4/1996 | Dow et al. |            |
|-----------|-----|---|--------|------------|------------|
| 5,906,988 | A   | * | 5/1999 | Dow et al. | 514/252.12 |
| 7,060,723 | B2  | * | 6/2006 | Ehring et al. | 514/438 |
| 2008/0234339 | A1 | * | 9/2008 | Weiss | 514/367 |

FOREIGN PATENT DOCUMENTS

WO    2007022568    3/2007

OTHER PUBLICATIONS

Naesch. O., et al , "Purine metabolite washout and platelet aggregation at reflow after tourniquet ischemia: Effect of intravenous regional lidocaine"ACTS Anaesthesiologica Scandinavica, 1995, vol. 39, No. 8, pp. 1053-1058.
Schmid, r.a., et al., "Lidocaine reduces reperfusion injury and neutrophil migration in canine lung allografts", Annals of Thoracic Surgery, 1999, vol. 61, No. 3, pp. 949-955.
Karacal, N., et al., "Enhancement of dorsal random-pattern skin flap survival in rats with topical lidocaine and prilocaine (EMLA): Enhancement of flap survival by EMLA", Journal of Surgical Research, 2005, vol. 124, No. 1, pp. 134-138.
Bakare, A., et al., "Mood stabilizing drgus lamotrigine olanzapine increase expression and activity of glutathione s-transferase in primary cultured rat cerebral cortex cells": Nerosceience Letters, 2009, vol. 455: No. 1, pp. 70-73.
Stevenson, A., et al., "Riluzole protects against glutamate-induced slowing of neurofilament sxonal transport". Neuroscience Letters. 2009, vol. 454, No. 2, pp. 161-164.
Toklu, H.Z., et al., "The effects of riluzole on neurological, brain biochemical, and histological changes in early and late term of sepsis in rats", Journal of Surgical Research, 2009, vol. 152, No. 2, pp. 238-248.
Ettaiche. M., et al, "Riluzole improves functional recovery after ischemia in the rat retina", 1999, Invest Opthamel Vis Sci, vol. 40, No. 3; pp. 729-736.
Kinasiewicz A , et al., "Lidocaine as a protective agent during pancreas cold ischemia", Acta Poloniae Pharmaceutica—Drug Research, vol. 57, No. 6, pp. 455-458.

* cited by examiner

*Primary Examiner* — Raymond Henley, III
(74) *Attorney, Agent, or Firm* — Honigman Miller Schwartz and Cohn; Thomas A. Wootton; Jonathan P. O'Brien

(57) ABSTRACT

The present invention relates to a method for slowing the development of mammalian organ, tissue and cellular damage and death by using a persistent sodium current blocker (or a pharmaceutically acceptable salt or derivative thereof). The present invention further relates to a method for preventing damage and death in mammalian organs, tissues and cells or reducing the extent of damage and death in mammalian organs, tissues and cells. In particular the invention relates to a method for the treatment, amelioration or prevention of non-neuronal and non-myocardial cell or tissue damage or death and for reducing the pain associated with non-neuronal and non-myocardial cell or tissue damage.

20 Claims, 6 Drawing Sheets

TREATMENT OF NON-NEURONAL AND NON-MYOCARDIAL CELL, TISSUE AND ORGAN DAMAGE AND ASSOCIATED PAIN WITH PERSISTENT SODIUM CURRENT BLOCKERS

This application is the U.S. National phase of PCT Application Serial No. PCT/AU2010/000814, filed Jun. 29, 2010, which claims the priority of Australian Provisional Application No. 2009903235, filed Jul. 9, 2009, both of which are incorporated herein by reference in their entirety.

FIELD OF THE INVENTION

The present invention relates to a method for slowing the development of mammalian organ, tissue and cellular damage and death. The present invention further relates to a method for preventing damage and death in mammalian organs, tissues and cells or reducing the extent of damage and death in mammalian organs, tissues and cells. In particular the invention relates to a method for the treatment, amelioration or prevention of non-neuronal and non-myocardial cell or tissue damage or death and for reducing the pain associated with non-neuronal and non-myocardial cell or tissue damage or death.

BACKGROUND OF THE INVENTION

There are many causes of organ, tissue and cell damage and death. The consequences of such damage and death in muscle, for example, include: muscular atrophy, reduced mobility, reduced smooth muscle function, compensation by other muscles, skeletal mal-alignment and deformity. Treatment for such organ, tissue and cell damage and death has so far been limited to: medications, surgery to attempt reperfusion and hyperbaric oxygen treatment. Of additional concern is that some of these treatments, and in particular the treatment of reperfusion, can lead to further organ, tissue and cell damage and death. An additional consequence of organ, tissue and cell damage and death is the associated pain. Many of the causes of organ, tissue and cell damage and death simultaneously promote pain. For example, hypoxia in many tissues creates oedema which separates cells within those tissues; the separation of cells generating immense pain.

Given the physiological limitations consequent upon organ, tissue and cell damage and death, as well as the limitations of the current treatments, it would be desirable to provide a treatment which could mitigate or even avert such damage and death arising from hypoxia, ischaemia, reperfusion, ischaemia-reperfusion injury, infarction, necrosis, free tissue transfer, organ transplant, certain diseases such as myopathy or muscular dystrophy, degenerative diseases such as chronic kidney disease or kidney failure, hypertrophy, inflammation, scarring, physical injuries, crush injuries, lacerations. tourniquet, certain medical interventions, certain surgical interventions or procedures, exposure to certain chemicals, toxins, bacteria, viruses or radiation, tissue reperfusion or other form of alteration to the normal function of the cells, tissues or organs.

SUMMARY OF THE INVENTION

Surprisingly, it has been discovered in accordance with the present invention, that persistent sodium current blockers may be effective in reducing non-neuronal and non-myocardial cell or tissue damage or death.

A first aspect of the invention provides for a method for the treatment, amelioration or prevention of non-neuronal and non-myocardial cell or tissue damage or death, comprising administering to a mammal in need thereof a therapeutically effective amount of a persistent sodium current blocker or a pharmaceutically acceptable salt or derivative thereof.

A second aspect of the invention provides for use of a persistent sodium current blocker or a pharmaceutically acceptable salt or derivative thereof in the manufacture of a medicament for the treatment, amelioration or prevention of non-neuronal and non-myocardial cell or tissue damage or death.

A third aspect of the invention provides for a persistent sodium current blocker or a pharmaceutically acceptable salt or derivative thereof for use in the treatment, amelioration or prevention of non-neuronal and non-myocardial cell or tissue damage or death.

An important facet of this invention is that persistent sodium channels in cells can be blocked without impacting upon cardiac transient sodium channels which are critical for the normal functioning of the heart.

DEFINITIONS

Figure 1:
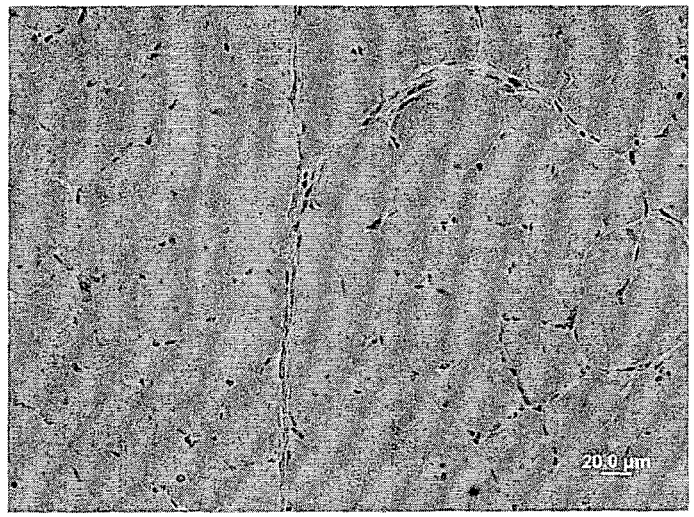
FIG. 1. A section of undamaged tibialis anterior muscle as viewed under a microscope.

The following are some definitions that may be helpful in understanding the description of the present invention. These are intended as general definitions and should in no way limit the scope of the present invention to those terms alone, but are put forth for a better understanding of the following description.

Unless the context requires otherwise or specifically stated to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including, but not necessarily solely including".

Those skilled in the art will appreciate that the invention described herein is susceptible to variations and modifications other than those specifically described. It is to be understood that the invention includes all such variations and modifications. The invention also includes all of the steps, features, compounds and compositions referred to or indicated in this specification, individually or collectively, and any and all combinations of any two or more of said steps, features, compounds and compositions.

All references cited in this application are specifically incorporated by cross-reference in their entirety. Reference to any such documents should not be construed as an admission that the document forms part of the common general knowledge or is prior art.

In the context of this specification, it is to be understood the term persistent sodium channel, as used herein, relates to any channel which permits a persistent sodium current to pass through a cell membrane. As such, the terms blocking a persistent sodium current and blocking a persistent sodium channel, are synonymous as used herein. It is further to be understood that the blocking of multiple persistent sodium channels is not an all-or-none phenomenon and therefore that different doses of persistent sodium channel blockers will block different numbers of persistent sodium channels.

In the context of this invention the term "administering" and variations of that term including "administer" and "administration", includes contacting, applying, delivering or providing a compound or composition of the invention to an organism, or a surface by any appropriate means.

In the context of this specification, the term "treatment", refers to any and all uses which remedy a disease state or symptoms, prevent the establishment of disease, or otherwise prevent, hinder, retard, or reverse the progression of disease or other undesirable symptoms in any way whatsoever.

In the context of this specification the term "therapeutically effective amount" includes within its meaning a sufficient but non-toxic amount of a compound or composition of the invention to provide the desired therapeutic effect. The exact amount required will vary from subject to subject depending on factors such as the species being treated, the age and general condition of the subject, the severity of the condition being treated, the particular agent being administered, the mode of administration, and so forth. Thus, it is not possible to specify an exact "therapeutically effective amount". However, for any given case, an appropriate "therapeutically effective amount" may be determined by one of ordinary skill in the art using only routine experimentation.

In the context of this specification it is to be understood that methods for identifying mammals in need of treatment, amelioration or prevention of non-neuronal and non-myocardial cell or tissue damage or death according to the present invention are known to those skilled in the art.

In the context of this specification it is to be understood that the term "free tissue transfer" includes within its scope "tissue grafts" and "tissue grafting"; "cell grafts", "cell transfer", "cell implantation" and "cell transfer grafting" as well as "organ transfer", "organ transfer grafts" and "organ transfer grafting".

In the context of this specification it is to be understood that the relative terms "reduce", "minimise", "enhance", "slow" and "increase" and variations of those terms including "reducing", "reduced", "minimising", "minimised", "enhancing", "enhanced", "slowing", "slowed", "increasing", and "increased" as they pertain to the present invention are to be read as being relative to the speed and/or extent of damage incurred, or recovery from, the amount of damage or recovery which would have occurred in the absence of the method of the present invention.

In the context of the specification it is to be understood that the term "derivative" includes within its scope the term and full meaning of the word "analogue".

In the context of the specification it is to be understood that the term "mammal" includes, but is not limited to, humans.

DETAILED DESCRIPTION OF EMBODIMENTS OF THE INVENTION

Numerous deleterious physiological and pathological conditions have been attributed to the persistent sodium current. These include: retinal ganglion disease, neuropathic pain, epilepsy, atrial fibrillation, convulsion, neurological ischaemia, cardiac arrhythmia, and myocardial damage.

While the existence of persistent sodium currents has been known for over 20 years, its relevance to treatment has been limited to various forms of neuronal and recently cardiac conditions. There has been no previous application of persistent sodium current blockers to skeletal or smooth muscle conditions, or for the treatment or prevention of organ or tissue cell damage or death outside of neuronal or cardiac conditions.

Tissue or cell damage can arise in a variety of circumstances, for example when the blood supply to the tissue or cell is restricted or lost (ischaemia) or when the blood is deprived of oxygen (hypoxia). Further damage can arise when the tissue or cell is reperfused. It has been found that the administration of a persistent sodium current blocker prior to reperfusion can prevent the cascade of cells to cell death or apoptosis. The application of a persistent sodium current blocker can also extend the period of ischaemia of the cells before damage results which can be beneficial in a number of circumstances including surgical procedures requiring the restriction of blood supply to particular cells or tissues.

Accordingly, one aspect of the invention provides for a method for the treatment, amelioration or prevention of non-neuronal and non-myocardial cell or tissue damage or death, comprising administering to a mammal in need thereof a therapeutically effective amount of a persistent sodium current blocker or a pharmaceutically acceptable salt or derivative thereof.

In one embodiment the persistent sodium current blocker is selected from the group consisting of riluzole, lidocaine or lamotrigine or a pharmaceutically acceptable salt or derivative thereof.

In one embodiment the non-neuronal and non-myocardial cell or tissue damage or death arises from any one of hypoxia, ischaemia, ischaemia-reperfusion injury, reperfusion, infarction, necrosis, free tissue transfer, organ transplant, disease, hypertrophy, inflammation, scarring, physical injuries, crush injuries, lacerations, tourniquet, medical interventions, surgical interventions or procedures, exposure to chemicals, toxins, bacteria, viruses or radiation, tissue reperfusion or other form of alteration to the normal function of the cells, tissues or organs.

In one embodiment the non-neuronal and non-myocardial cell or tissue damage or death arises from hypoxia, ischaemia, reperfusion or ischaemia-reperfusion injury. In another embodiment the non-neuronal and non-myocardial cell or tissue damage or death arises from physical injuries, crush injuries, lacerations, tourniquet, medical interventions, or surgical interventions or procedures. In another embodiment the non-neuronal and non-myocardial cell or tissue damage or death arises from physical injuries, crush injuries or lacerations. In a further embodiment the non-neuronal and non-myocardial cell or tissue damage or death arises from medical interventions or surgical interventions or procedures. In one embodiment the surgical procedure is an orthopaedic surgical procedure. In another embodiment the non-neuronal and non-myocardial cell or tissue damage or death arises from diseases such as myopathy or muscular dystrophy or degenerative diseases such as chronic kidney disease or kidney failure; degenerative visual conditions, degenerative hearing loss.

In one embodiment the non-neuronal and non-myocardial cell or tissue damage or death occurs in an organ selected from the group consisting of skeletal muscle, kidney, liver, lungs, pancreas, intestines, thymus, reproductive organs, oesophagus, stomach, gallbladder, urinary bladder, ureter, skin, spleen, eyes, ears, larynx and bones. In another embodiment the non-neuronal and non-myocardial cell or tissue damage or death occurs in an organ selected from the group consisting of skeletal muscle, kidney, liver, lungs, pancreas, skin, intestines, and thymus. In a further embodiment the cell or tissue damage or death occurs in the kidney.

It is important to note that cells which become damaged or which die as a result of a damaging event, do so at different rates to each other. As such, damaged regions of tissue will likely include a combination of healthy, damaged and dead cells. Therefore a compound which inhibits or prevents the damage or death of those cells could reduce the density of damaged tissue within these damaged regions.

Accordingly, in a further embodiment of the method of the present invention, the density of the damaged cells in the tissue is reduced.

It is similarly important to note that many cells recover from the damage caused to them. Therefore a compound which reduces or prevents damage or death of those cells will likely enhance the cellular recovery of the tissue and organs.

Accordingly, in a further embodiment of the method of the present invention, the recovery of the damaged cells in the tissue is enhanced.

Yet further, it is important to note that when a compound which inhibits or prevents the damage or death of cells is administered in anticipation of a damaging event, such as in anticipation of reperfusion, it will likely provide protection against cellular damage or death which may arise.

Accordingly, in a further embodiment of the method of the present invention, cells and tissue are protected from becoming damaged during reperfusion.

Also, it is important to note that reducing the speed of tissue and cellular degradation maintains organ viability and functionality for longer and hence also maintains quality of life and in some cases longevity, for longer. For example, reducing the speed of degradation of muscle in diseases such as muscular dystrophy maintains muscle viability and functionality for longer and hence also maintains quality of life for longer.

Accordingly, in a further embodiment of the method of the present invention, the speed or extent of degradation of the non-neuronal and non-myocardial cell or tissue damage or death is reduced.

In addition to the above is the concept of the border zone. The border zone is described as being composed of interdigitatingx ischemic and non-ischemic tissues. The border zone is the zone of tissue surrounding or adjacent to an hypoxic, ischaemic or otherwise damaged region of tissue. The border zone is of clinical significance because a pharmaceutical composition which can cause the inside border of the border zone to infiltrate the damaged region, could reduce the volume of the damaged region to a volume sufficiently small to become clinically insignificant.

Furthermore, a consequence of reducing the size of the inside border of a border zone and hence reducing the speed or extent of development of the damaged region, is a reduction in the volume of non-viable tissue and hence a relative increase in the efficiency of the tissue.

Similarly, a pharmaceutical composition which can reduce the size of the outside border of the border zone can reduce the volume of the border zone and subsequently the overall density of cell damage and cell death, possibly to a volume sufficiently small to become clinically insignificant.

As with the inside border of a border zone, a consequence of reducing the size of the outside border of a border zone and hence reducing the speed or extent of development of the damaged region, is a reduction in the volume of non-viable tissue and hence a relative increase in the efficiency of the tissue.

Reducing the speed or extent of development of cell damage or cell death either within a damaged region of tissue or within the border zones, reduces the density of damaged cells in the tissue. Reducing the density of damaged cells in the tissue reduces the deleterious effects such cell damage or cell death can have on the efficiency of the tissue. This is particularly important for tissue which impacts upon other organs, for example, muscles which control other system functions such as respiration or blood pressure.

Accordingly, in a further embodiment of the method of the present invention, the size or volume of a damaged region or the density of cellular damage in a damaged region in non-neuronal and non-myocardial cells or tissues is reduced. In another embodiment, the size or volume of a border zone or the size of the inside border of a border zone or the size of an outside border of a border zone or the density of cellular damage in a border zone surrounding a damaged region is reduced.

Furthermore, reducing the speed or extent of development of cell damage or cell death increases the recovery both in terms of the time taken for the muscle efficiency to recover and in terms of the speed or extent of recovery of the muscle tissue.

Accordingly, in a further embodiment of the method of the present invention, the speed of development of the non-neuronal and non-myocardial cell or tissue damage or death is reduced. In another embodiment the extent of the damage or death of non-neuronal and non-myocardial cells or tissues is reduced. In another embodiment, the speed or extent of recovery of non-neuronal and non-myocardial cell or tissue damage is aided.

While a few damaged cells may spontaneously recover following a damage causing event, many have the opportunity to recover following re-establishment of blood flow through the tissue (reperfusion). Hence the administration of a compound which reduces the speed or extent of cell damage or cell death significantly increases the opportunity for recovery when combined with reperfusion.

Accordingly, in a further embodiment of the method of the present invention, the opportunity for recovery when combined with reperfusion is enhanced by reducing the speed or extent of degradation of the non-neuronal and non-myocardial cell or tissue damage or death.

In one embodiment of the method of the present invention, the speed of development of non-neuronal and non-myocardial cell or tissue damage or death is reduced, or the speed of degradation of non-neuronal and non-myocardial cell or tissue damage is reduced, or the speed of recovery of non-neuronal and non-myocardial cell or tissue damage is enhanced.

In one embodiment the persistent sodium current blocker is selected from the group comprising lidocaine, mexiletine, lamotrigine, BW1003C87 ([5-(2,3,5-trichlorophenyl)pyrimidine-2,4-diamine 1.1 ethanesulphonate]), sipatrigine, phenytoin, fosphenytoin, riluzole, benzothiazole derivatives, ranolazine, flunarizine, CP-060S ((−)-(S)-2-[3,5-bis(1,1-dimethylethyl)-4-hydroxyphenyl]-3-[3-[N-methyl-N-[2-(3,4-methylenedioxyphenoxy)ethyl]amino]propyl]-1,3-thiazolidin-4-one hydrogen fumarate), R56865 (N-[1-(4-(4-fluorophenoxy)butyl)]-4-piperidinyl-N-methyl-2-benzothiazolamine), flecainide, azure A, veratridine, CNS 5546A, N-methylstrychnine, and F15845 (3-(R)-[3-(2-methoxyphenylthio-2-(S)-methylpropyl]amino-3,4-dihydro-2H-1,5-benzoxathiepine bromohydrate) or a pharmaceutically acceptable salt or derivative thereof.

Riluzole (2-amino-6-trifluoromethoxybenzothiazole), for example, which has the following structure:

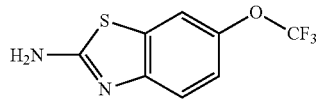

is described as a treatment for amyotrophic lateral sclerosis (ALS), a degenerative neuronal disease unrelated to hypoxia, ischaemia, infarction, necrosis, free tissue transfer, organ transplant, certain diseases such as myopathy or muscular dystrophy, hypertrophy, inflammation, scarring, physical injuries, crush injuries, lacerations, tourniquet, medical interventions, certain surgical interventions or procedures, exposure to chemicals, toxins, bacteria, viruses or radiation, reperfusion or other form of alteration to the normal function of non-neuronal and non-myocardial cells or tissues. Riluzole has also been found to be useful as an anticonvulsant, an anxiolytic and a hypnotic, in the treatment of schizophrenia, in the treatment of sleep disorders and of depression, in the treatment of cerebrovascular disorders and as an anaesthetic, in the treatment of spinal, cranial or cranio-spinal traumas, in the treatment of Parkinson's disease, and in the treatment of mitochondrial diseases. More recently, riluzole has been identified as a persistent sodium channel blocker for use in preventing optic nerve degeneration associated with glaucoma and as a persistent sodium channel blocker in rat cortical neurons. All of these described uses for riluzole are confined to the treatment of neuronal conditions.

Riluzole has also been described as a drug for treating cardiac arrhythmias and myocardial damage, however, as already described, there has not yet been any suggestion that riluzole could treat non-neuronal and non-cardiac cell, tissue and organ damage or death.

Accordingly, in a further embodiment of the method of the present invention, the persistent sodium current blocker is riluzole or a pharmaceutically acceptable salt or derivative thereof.

In another embodiment the persistent sodium current blocker is selected from the group comprising riluzole, benzothiazole derivatives, lidocaine, lamotrigine, fosphenytoin, mexiletine, phenytoin, ranolazine, BW1003C87 ([5-(2,3,5-trichlorophenyl)pyrimidine-2,4-diamine 1.1 ethanesulphonate]), sipatrigine and R56865 (N-[1-(4-(4-fluorophenoxy)butyl)]-4-piperidinyl-N-methyl-2-benzo-thiazolamine) or a pharmaceutically acceptable salt or derivative thereof. In a further embodiment the persistent sodium current blocker is selected from the group comprising riluzole, lidocaine, lamotrigine, and fosphenytoin or a pharmaceutically acceptable salt or derivative thereof. In another embodiment the persistent sodium current blocker is selected from the group comprising riluzole and lidocaine or a pharmaceutically acceptable salt or derivative thereof. In another embodiment the persistent sodium current blocker is selected from the group comprising lidocaine, lamotrigine and riluzole or a pharmaceutically acceptable salt or derivative thereof. In a further embodiment the persistent sodium current blocker is selected from the group comprising lidocaine, lamotrigine, and fosphenytoin or a pharmaceutically acceptable salt or derivative thereof.

In one embodiment of the methods of the present invention, the method is for the treatment, amelioration or prevention of non-neuronal and non-myocardial cell or tissue damage or death in skeletal muscle tissue, smooth muscle tissue, connective tissue or epithelial tissue. In one embodiment of the methods of the present invention, the method is for the treatment, amelioration or prevention of non-neuronal and non-myocardial cell or tissue damage or death in skeletal muscle tissue or smooth muscle tissue. In another embodiment of the methods of the present invention, the method is for the treatment, amelioration or prevention of non-neuronal and non-myocardial cell or tissue damage or death in skeletal muscle tissue. In another embodiment the method is for the treatment, amelioration or prevention of non-neuronal and non-myocardial cell or tissue damage or death in smooth muscle tissue. In a further embodiment of the methods of the present invention, the method is for the treatment, amelioration or prevention of non-neuronal and non-myocardial cell or tissue damage or death in connective tissue or epithelial tissue. In another embodiment the method is for the treatment, amelioration or prevention of cell or tissue damage or death in connective tissue. In a further embodiment the method is for the treatment, amelioration or prevention of non-neuronal and non-myocardial cell or tissue damage or death in epithelial tissue. In another embodiment the method is for the prevention of cell damage or death in skeletal muscle tissue. In a further embodiment the method for is for the treatment of cell damage or death in skeletal muscle tissue. In another embodiment the method is for the prevention of cell damage or death in smooth muscle tissue. In a further embodiment the method is for the treatment of cell damage or death in smooth muscle tissue.

In a further embodiment of the present invention, the non-neuronal and non-myocardial cell or tissue damage or death is associated with free tissue transfer or organ transplant. In one embodiment the non-neuronal and non-myocardial cell or tissue damage or death is associated with free tissue transfer. In another embodiment the non-neuronal and non-myocardial cell or tissue damage or death is associated with organ transplant. In one embodiment the organ to be transplanted is treated prior to or during or post transfer or transplant with a therapeutically effective amount of a persistent sodium current blocker or a pharmaceutically acceptable salt or derivative thereof.

In one embodiment the organ to be transplanted is selected from the group consisting of skeletal muscle, lungs, heart, kidney, urinary bladder, ureter, esophagus, stomach, intestine, liver, spleen, pancreas, skin, bone, eye, and thymus. In another embodiment the organ to be transplanted is a kidney.

In one embodiment the free tissue to be transferred is selected from the group consisting of skeletal muscle tissue, smooth muscle tissue, connective tissue, epithelial tissue, skin, subcutaneous tissue, fat and adipose tissue, bone, blood vessels, lymphatic vessels and reproductive tissue including germ cells.

In a further embodiment the non-neuronal and non-myocardial cell or tissue damage or death is due to a loss or reduction in blood or oxygen supply.

In a further embodiment the non-neuronal and non-myocardial tissue or cellular damage or death is due to a loss or reduction in blood or oxygen supply associated with: disease, hypertrophy, inflammation, scarring, physical injuries, crush injuries, lacerations, tourniquet, medical interventions and surgical interventions or procedures.

In a further embodiment, the non-neuronal and non-myocardial tissue or cellular death or damage is due to a resumption or partial resumption of blood or oxygen supply.

A direct relationship exists between the damage to non-neuronal and non-myocardial cells and tissues and the pain which arise from that damage. For example, hypoxia in many tissues creates oedema which separates cells within those tissues; the separation of cells generating immense pain. The application of a tourniquet in surgery is a further example of the production of tissue ischaemia and hypoxia. Patients who are conscious are only able to tolerate tourniquet application for short periods of time. Patients who have tourniquets applied for prolonged periods while under general anaesthesia require high doses of analgesia following the procedure.

Accordingly, a further embodiment of the invention provides for a method for reducing pain associated with non-neuronal and non-myocardial cell or tissue damage or death due to a loss or reduction in blood or oxygen supply. Reduction in pain may be assessed by instruments such as a patient derived pain score or by recording the total analgesic (for example—morphine or opiate) dosage required post such an ischaemic or hypoxic insult.

In a further embodiment the invention provides for a method for the prevention or amelioration of ischaemia-reperfusion injury in non-neuronal and non-myocardial cells, or tissues comprising administering to a mammal in need thereof a therapeutically effective amount of a persistent sodium current blocker or a pharmaceutically acceptable salt or derivative thereof. In one embodiment, the persistent sodium current blocker is riluzole or a pharmaceutically acceptable salt or derivative thereof.

In a preferred embodiment the mammal is a human.

The invention also relates to the use of persistent sodium current blockers in the manufacture of a medicament for treating, ameliorating or preventing non-neuronal and non-myocardial cellular or tissue damage or death.

Accordingly, a further aspect of the invention provides for use of a persistent sodium current blocker or a pharmaceutically acceptable salt or derivative thereof in the manufacture of a medicament for the treatment, amelioration or prevention of non-neuronal and non-myocardial cell or tissue damage or death.

In one embodiment the persistent sodium current blocker is selected from the group consisting of riluzole, lidocaine or lamotrigine or a pharmaceutically acceptable salt or derivative thereof. In a further embodiment, the persistent sodium current blocker is riluzole or a pharmaceutically acceptable salt or derivative thereof.

In another embodiment the invention provides for use of a persistent sodium current blocker or a pharmaceutically acceptable salt or derivative thereof in the manufacture of a medicament for the treatment, prevention or amelioration of non-neuronal and non-myocardial cellular or tissue damage or death due to a loss of blood or oxygen supply.

In a further embodiment the invention provides for use of a persistent sodium current blocker or a pharmaceutically acceptable salt or derivative thereof in the manufacture of a medicament for the treatment, prevention or amelioration of ischaemia-reperfusion injury in non-neuronal and non-myocardial cells or tissues.

In a further embodiment the invention provides for use of a persistent sodium current blocker or a pharmaceutically acceptable salt or derivative thereof in the manufacture of a medicament for the treatment, prevention or amelioration of non-neuronal and non-myocardial tissue or cellular damage or death due to a loss or reduction in blood or oxygen supply associated with disease, hypertrophy, inflammation, scarring, physical injuries, crush injuries, lacerations, tourniquet, certain medical interventions and certain surgical interventions or procedures.

A further embodiment of the invention provides for use of a persistent sodium current blocker or a pharmaceutically acceptable salt or derivative thereof in the manufacture of a medicament for the reduction of pain associated with non-neuronal and non-myocardial cell or tissue damage or death due to a loss or reduction in blood or oxygen supply. In one embodiment the pain associated with non-neuronal and non-myocardial cell or tissue damage or death is reduced.

Organ Transplant

Organ transplant is the moving of an organ from one body to another for the purpose of replacing a recipient's damaged or failing organ with a functioning organ from a donor site. The transplanting of an organ results in a period of ischaemia or lack of blood supply, during which time damage can be sustained to the tissues and cells surrounding the transplant site and within the transplanted organ. The administration of a persistent sodium current blocker could result in an increase in the ischaemia time which is tolerated and a reduction in the damage sustained to the cells and tissues and to the organ itself during ischaemia and during subsequent reperfusion.

Accordingly, a further embodiment of the invention provides for a method for treating, preventing or ameliorating non-neuronal and non-myocardial tissue or cellular damage or death due to a loss or reduction in blood or oxygen supply associated with organ transplants, comprising administering to a mammal in need thereof a therapeutically effective amount of a persistent sodium current blocker or a pharmaceutically acceptable salt or derivative thereof.

In one embodiment the organ to be transplanted is treated prior to or during or post transplantation with a therapeutically effective amount of a persistent sodium current blocker or a pharmaceutically acceptable salt thereof.

In one embodiment the organ to be transplanted is selected from the group consisting of skeletal muscle, lungs, heart, kidney, urinary bladder, ureter, esophagus, stomach, intestine, liver, spleen, pancreas, skin, bone, eye, and thymus. In one embodiment the organ to be transplanted is selected from the group consisting of kidney, liver, heart, lungs, pancreas, skin, intestines and thymus. In one embodiment the organ to be transplanted is selected from the group consisting of kidney, liver, lungs, pancreas, skin, intestines and thymus. In a further embodiment the organ to be transplanted is a kidney.

In one embodiment the persistent sodium current blocker is selected from the group comprising lidocaine, benzothiazole derivatives, mexiletine, lamotrigine, BW1003C87 ([5-(2,3,5-trichlorophenyl)pyrimidine-2,4-diamine 1.1 ethanesulphonate]), sipatrigine, phenytoin, fosphenytoin, riluzole, ranolazine, flunarizine, CP-060S ((−)-(S)-2-[3,5-bis(1,1-dimethylethyl)-4-hydroxyphenyl]-3-[3-[N-methyl-N-[2-(3, 4-methylenedioxyphenoxy)ethyl]amino]propyl]-1,3-thiazolidin-4-one hydrogen fumarate), R56865 (N-[1-(4-(4-fluorophenoxy)butyl)]-4-piperidinyl-N-methyl-2-benzo-thiazolamine), flecainide, azure A, veratridine, CNS 5546A, N-methylstrychnine, and F15845 (3-(R)-[3-(2-methoxyphenylthio-2-(S)-methylpropyl]amino-3,4-dihydro-2H-1,5-benzoxathiepine bromohydrate) or a pharmaceutically acceptable salt or derivative thereof.

In a further embodiment the persistent sodium current blocker is riluzole or a pharmaceutically acceptable salt or derivative thereof.

In another embodiment the persistent sodium current blocker is selected from the group comprising riluzole, benzothiazole derivatives, lidocaine, lamotrigine, fosphenytoin, mexiletine, phenytoin, ranolazine, BW1003C87 ([5-(2,3,5-trichlorophenyl)pyrimidine-2,4-diamine 1.1 ethanesulphonate]), sipatrigine, and R56865 (N-[1-(4-(4-fluorophenoxy)butyl)]-4-piperidinyl-N-methyl-2-benzo-thiazolamine) or a pharmaceutically acceptable salt or derivative thereof. In a further embodiment the persistent sodium current blocker is selected from the group comprising riluzole, lidocaine, lamotrigine, and fosphenytoin or a pharmaceutically acceptable salt or derivative thereof. In another embodiment the persistent sodium current blocker is selected from the group comprising riluzole and liodcaine or a pharmaceutically acceptable salt or derivative thereof. In another embodiment the persistent sodium current blocker is selected from the group comprising lidocaine, lamotrigine and riluzole or a pharmaceutically acceptable salt or derivative thereof. In a further embodiment the persistent sodium current blocker is selected from the group comprising lidocaine, lamotrigine, and fosphenytoin or a pharmaceutically acceptable salt or derivative thereof.

A further embodiment of the invention provides for the use of a persistent sodium current blocker or a pharmaceutically acceptable salt or derivative thereof in the manufacture of a medicament for the treatment, prevention or amelioration of non-neuronal and non-myocardial tissue or cellular damage or death due to a loss or reduction in blood or oxygen supply associated with organ transplants.

Free-Tissue Transfer

Free tissue transfer is the vascular detachment of an isolated and specific region of the body (eg, skin, fat, muscle, bone) followed by transfer of that tissue to another region of the body with reattachment of the divided artery and vein to separate artery and vein. This naturally results in a period of ischaemia with the blood supply to the tissue being disrupted. The tolerated ischaemia times will depend on the composition of the tissue to be transferred, however in general a maximum of 2 to 3 hours will be tolerated. The administration of a persistent sodium current blocker could result in an increase in the ischaemia time which is tolerated and a reduction in the damage sustained to the cells and tissues.

Accordingly, a further embodiment of the invention provides for a method for preventing or ameliorating non-neuronal and non-myocardial tissue or cellular damage or death due to a loss or reduction in blood or oxygen supply associated with free tissue transfer, comprising administering to a mammal in need thereof a therapeutically effective amount of a persistent sodium current blocker or a pharmaceutically acceptable salt or derivative thereof.

In one embodiment the free tissue to be transferred is selected from the group consisting of skeletal muscle tissue, smooth muscle tissue, connective tissue, epithelial tissue, skin, subcutaneous tissue, fat and adipose tissue, bone, blood vessels, lymphatic vessels and reproductive tissue including germ cells.

In one embodiment the persistent sodium current blocker is selected from the group comprising lidocaine, benzothiazole derivatives, mexiletine, lamotrigine, BW1003C87 ([5-(2,3,5-trichlorophenyl)pyrimidine-2,4-diamine 1.1 ethanesulphonate]), sipatrigine, phenytoin, fosphenytoin, riluzole, ranolazine, flunarizine, CP-060S ((−)-(S)-2-[3,5-bis(1,1-dimethylethyl)-4-hydroxyphenyl]-3-[3-[N-methyl-N-[2-(3, 4-methylenedioxyphenoxy)ethyl]amino]propyl]-1,3-thiazolidin-4-one hydrogen fumarate), R56865 (N-[1-(4-(4-fluorophenoxy)butyl)]-4-piperidinyl-N-methyl-2-benzo-thiazolamine), flecainide, azure A, veratridine, CNS 5546A, N-methylstrychnine, and F15845 (3-(R)-[3-(2-methoxyphenylthio-2-(S)-methylpropyl]amino-3,4-dihydro-2H-1,5-benzoxathiepine bromohydrate) or a pharmaceutically acceptable salt or derivative thereof.

In one embodiment the persistent sodium current blocker is riluzole or a pharmaceutically acceptable salt or derivative thereof.

In another embodiment the persistent sodium current blocker is selected from the group comprising riluzole, lidocaine, lamotrigine, fosphenytoin, mexiletine, phenytoin, ranolazine, ([5-(2,3,5-trichlorophenyl)pyrimidine-2,4-diamine 1.1 ethanesulphonate]), sipatrigine and R56865 (N-[1-(4-(4-fluorophenoxy)butyl)]-4-piperidinyl-N-methyl-2-benzo-thiazolamine) or a pharmaceutically acceptable salt or derivative thereof. In a further embodiment the persistent sodium current blocker is selected from the group comprising riluzole, lidocaine, lamotrigine, and fosphenytoin or a pharmaceutically acceptable salt or derivative thereof. In another embodiment the persistent sodium current blocker is selected from the group comprising riluzole and liodcaine or a pharmaceutically acceptable salt or derivative thereof. In another embodiment the persistent sodium current blocker is selected from the group comprising lidocaine, lamotrigine and riluzole or a pharmaceutically acceptable salt or derivative thereof. In a further embodiment the persistent sodium current blocker is selected from the group comprising lidocaine, lamotrigine, and fosphenytoin or a pharmaceutically acceptable salt or derivative thereof.

A further embodiment of the invention provides for the use of a persistent sodium current blocker or a pharmaceutically acceptable salt or derivative thereof in the manufacture of a medicament for the prevention or amelioration of non-neuronal and non-myocardial tissue or cellular damage or death due to a loss or reduction in blood or oxygen supply associated with free tissue transfer.

Compounds utilised in accordance with the present invention may be administered prophylactically prior to expected tissue damage, such as a sports injury, surgery, transplant or reperfusion; during a tissue damaging event such as surgery, transplant, transfer or reperfusion; or following a tissue damaging event such as a sports injury.

Formulations

In accordance with the present invention, when used for the treatment or prevention of organ, tissue or cellular damage or death, persistent sodium current blockers of the invention may be administered alone. Alternatively, the persistent sodium current blockers may be administered as a pharmaceutical or veterinarial formulation which comprises at least one persistent sodium current blocker according to the invention. The persistent sodium current blockers may also be present as suitable salts, including pharmaceutically acceptable salts. Derivatives of the persistent sodium current blockers may also be used. Derivatives of the persistent sodium current blockers in addition to salts include, but are not limited to, solvates and hydrates of the persistent sodium current blockers.

By pharmaceutically acceptable salt it is meant those salts which, within the scope of sound medical judgement, are suitable for use in contact with the tissues of humans and lower animals without undue toxicity, irritation, allergic response and the like, and are commensurate with a reasonable benefit/risk ratio. Pharmaceutically acceptable salts are well known in the art and include acid addition and base salts. Hemisalts of acids and bases may also be formed.

For persistent sodium current blockers having a basic site, suitable pharmaceutically acceptable salts may be acid addition salts. For example, suitable pharmaceutically acceptable salts of such compounds may be prepared by mixing a pharmaceutically acceptable acid such as hydrochloric acid, sulfuric acid, methanesulfonic acid, succinic acid, fumaric acid, maleic acid, benzoic acid, phosphoric acid, acetic acid, oxalic acid, carbonic acid, tartaric acid, or citric acid with the persistent sodium current blockers of the invention.

S. M. Berge et al. describe pharmaceutically acceptable salts in detail in *J. Pharmaceutical Sciences,* 1977, 66:1-19. The salts can be prepared in situ during the final isolation and purification of the compounds of the invention, or separately by reacting the free base function with a suitable organic acid. Representative acid addition salts include acetate, adipate, alginate, ascorbate, asparate, benzenesulfonate, benzoate, bisulfate, borate, butyrate, camphorate, camphorsulfonate, citrate, digluconate, cyclopentanepropionate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Suitable base salts are formed from bases that form non-toxic salts. Examples include the aluminium, arginine, benzathine, calcium, choline, diethylamine, diolamine, glycine, lysine, magnesium, meglumine, olamine, potassium, sodium, tromethamine and zinc salts. Representative alkali or alkaline earth metal salts include sodium, lithium potassium, calcium, magnesium, and the like, as well as non-toxic ammonium, quaternary ammonium, and amine cations, including, but not limited to ammonium, tetramethylammonium, tetraethylammonium, methylamine, dimethylamine, trimethylamine, triethylamine, ethylamine, triethanolamine and the like.

Pharmaceutically acceptable salts of persistent sodium current blocking compounds may be prepared by methods known to those skilled in the art, including:
(i) reacting the compound with the desired acid or base;
(ii) removing an acid- or base-labile protecting group from a suitable precursor of the compound or by ring-opening a suitable cyclic precursor, for example, a lactone or lactam, using the desired acid or base; or
(iii) converting one salt of the compound to another by reaction with an appropriate acid or base or by means of a suitable ion exchange column.

The above reactions (i)-(iii) are typically carried out in solution. The resulting salt may precipitate out and be collected by filtration or may be recovered by evaporation of the solvent. The degree of ionisation in the resulting salt may vary from completely ionised to almost non-ionised.

The persistent sodium current blockers of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when the solvent is water.

In accordance with the present invention, the persistent sodium current blockers of the invention may be used in combination with other known treatments or antimicrobial agents, including antibiotics. Suitable agents are listed, for example, in the Merck Index, *An Encyclopaedia of Chemicals, Drugs and Biologicals,* $12^{th}$ Ed., 1996, the entire contents of which are incorporated herein by reference.

Modes of Administration

Convenient modes of administration include injection (subcutaneous, intravenous, intramuscular, intraperitoneal, etc.), oral administration, inhalation, transdermal application, topical creams or gels or powders, implantable drug pumps or rectal administration. Depending on the route of administration, the formulation and/or persistent sodium current blockers may be coated with a material to protect the compound from the action of enzymes, acids and other natural conditions which may inactivate the therapeutic activity of the compound. The persistent sodium current blockers may also be administered parenterally or intraperitoneally.

Dispersions of the persistent sodium current blockers according to the invention may also be prepared in glycerol, liquid polyethylene glycols, or propylene glycol and mixtures thereof and in oils. Under ordinary conditions of storage and use, pharmaceutical preparations may contain a preservative to prevent the growth of microorganisms.

Pharmaceutical compositions suitable for injection include sterile aqueous solutions (where water soluble) or dispersions and sterile powders for the extemporaneous preparation of sterile injectable solutions or dispersions. Ideally, the composition is stable under the conditions of manufacture and storage and may include a preservative to stabilise the composition against the contaminating action of microorganisms such as bacteria and fungi.

In one embodiment of the invention, the persistent sodium current blockers of the invention may be administered orally, for example, with an inert diluent or an assimilable edible carrier. The persistent sodium current blockers and other ingredients may also be enclosed in a hard or soft shell gelatin capsule, compressed into tablets, or incorporated directly into an individual's diet. For oral therapeutic administration, the persistent sodium current blockers may be incorporated with excipients and used in the form of ingestible tablets, buccal tablets, troches, capsules, elixirs, suspensions, syrups, wafers, and the like. Suitably, such compositions and preparations may contain at least 1% by weight of active compound. The percentage of the persistent sodium current blockers in pharmaceutical compositions and preparations may, of course, be varied and, for example, may conveniently range from about 2% to about 90%, about 5% to about 80%, about 10% to about 75%, about 15% to about 65%; about 20% to about 60%, about 25% to about 50%, about 30% to about 45%, about 35% to about 45%, about 2% to about 20%, about 5% to 20%, about 5% to 15%, or about 5% to 10% of the weight of the dosage unit. The amount of persistent sodium current blocker in therapeutically useful compositions is such that a suitable dosage will be obtained.

The language "pharmaceutically acceptable carrier" is intended to include solvents, dispersion media, coatings, antibacterial and anti-fungal agents, isotonic and absorption delaying agents, and the like. The use of such media and agents for pharmaceutically active substances is well known in the art. Except insofar as any conventional media or agent is incompatible with the compound, use thereof in the therapeutic compositions and methods of treatment and prophylaxis is contemplated. Supplementary active compounds may also be incorporated into the compositions according to the present invention. It is especially advantageous to formulate parenteral compositions in dosage unit form for ease of administration and uniformity of dosage. "Dosage unit form" as used herein refers to physically discrete units suited as unitary dosages for the individual to be treated; each unit containing a predetermined quantity of compound(s) is calculated to produce the desired therapeutic effect in association with the required pharmaceutical carrier. The compound(s) may be formulated for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

In one embodiment, the carrier may be an orally administrable carrier.

Another form of a pharmaceutical composition is a dosage form formulated as enterically coated granules, tablets or capsules suitable for oral administration.

Also included in the scope of this invention are delayed release formulations, sustained release formulations, modified release formulations, controlled release formulations and repeat-action dosage forms.

Persistent sodium current blockers of the invention may also be administered in the form of a "prodrug". A prodrug is an inactive form of a compound which is transformed in vivo to the active form. Suitable prodrugs include esters, phosphonate esters etc, of the active form of the compound.

In one embodiment, the persistent sodium current blocker may be administered by injection. In the case of injectable solutions, the carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by including various anti-bacterial and/or anti-fungal agents. Suitable agents are well known to those skilled in the art and include, for example, parabens, chlorobutanol, phenol, benzyl alcohol, ascorbic acid, thimerosal, and the like. In many cases, it may be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminium monostearate and gelatin.

Sterile injectable solutions can be prepared by incorporating the analogue in the required amount in an appropriate solvent with one or a combination of ingredients enumerated above, as required, followed by filtered sterilisation. Generally, dispersions are prepared by incorporating the analogue into a sterile vehicle which contains a basic dispersion medium and the required other ingredients from those enumerated above.

Tablets, troches, pills, capsules and the like can also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavouring agent such as peppermint, oil of wintergreen, or cherry flavouring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the analogue, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the analogue can be incorporated into sustained-release preparations and formulations.

Preferably, the pharmaceutical composition may further include a suitable buffer to minimise acid hydrolysis. Suitable buffer agent agents are well known to those skilled in the art and include, but are not limited to, phosphates, citrates, carbonates and mixtures thereof.

Dosage

Single or multiple administrations of the persistent sodium current blockers according to the invention may be carried out. Similarly, single or multiple routes of administration may be carried out. One skilled in the art would be able, by routine experimentation, to determine effective, non-toxic dosage levels and routes of administration of the persistent sodium current blocker of the invention and an administration pattern which would be suitable for treating the diseases and/or infections to which the persistent sodium current blockers are applicable.

Further, it will be apparent to one of ordinary skill in the art that the optimal course of treatment, such as the number of doses of the persistent sodium current blocker of the invention given per day for a defined number of days, can be ascertained using conventional course of treatment determination tests.

Generally, an effective dosage per 24 hours may be in the range of about 0.0001 mg to about 1000 mg per kg body weight; suitably, about 0.001 mg to about 750 mg per kg body weight; about 0.01 mg to about 500 mg per kg body weight; about 0.1 mg to about 500 mg per kg body weight; about 0.1 mg to about 250 mg per kg body weight; or about 1.0 mg to about 250 mg per kg body weight. More suitably, an effective dosage per 24 hours may be in the range of about 1.0 mg to about 200 mg per kg body weight; about 1.0 mg to about 100 mg per kg body weight; about 1.0 mg to about 50 mg per kg body weight; about 1.0 mg to about 25 mg per kg body weight; about 5.0 mg to about 50 mg per kg body weight; about 5.0 mg to about 20 mg per kg body weight; about 5.0 mg to about 15 mg per kg body weight, about 0.1 mg to about 20 mg per kg body weight, about 0.1 mg to about 10 mg per kg body weight, about 0.2 mg to about 10 mg per kg body weight, about 0.5 mg to about 10 mg per kg body weight, or about 0.5 mg to about 5 mg per kg body weight.

Alternatively, an effective dosage may be up to about 500 mg/m². For example, generally, an effective dosage is expected to be in the range of about 5 to about 500 mg/m², about 25 to about 350 mg/m², about 25 to about 300 mg/m², about 25 to about 250 mg/m², about 5 to about 150 mg/m², about 10 to about 100 mg/m², about 10 to about 50 mg/m², about 50 to about 250 m g/m², and about 75 to about 150 mg/m². The effective dosage may be administered in single or multiple dose regimes per day dependent on factors such as pharmacokinetics of the agent/s in question and the specific indication or intervention.

The following examples demonstrate the invention and are not intended to be limiting to the overall scope of the invention.

EXAMPLES

Studies on Skeletal Muscles in Pigs

Studies were performed on both left and right tibialis anterior skeletal muscles in 22 isoflurane-anaesthetised, landrace or large white pigs (either sex, 20-35 kg). In all animals, Riluzole at 2 mg/kg (in the treated groups) or saline (in the control non-treated groups) was infused intravenously over ten minutes. A further ten minutes was allowed for drug circulation prior to the induction of ischaemia. Tissue ischaemia was produced by occluding the femoral artery. Immediately following occlusion, a 1,000 unit bolus of IV heparin was injected under mild force into the distal artery to prevent blood clotting and permit reperfusion. Occlusion was maintained for 3 hours following which, in the reperfusion groups, the occlusion was released and reperfusion of the muscle was allowed. Samples of reperfused tissue were excised 45 minutes following reperfusion. Samples of non-reperfused ischaemic tissue were excised 3 hours post occlusion. Samples of ischaemic tissue and of reperfused tissue were not taken from the same muscle. Samples of non-ischaemic tissue were excised 3 hours post occlusion of the alternate tibialis anterior muscle.

Example 1

Figure 2:
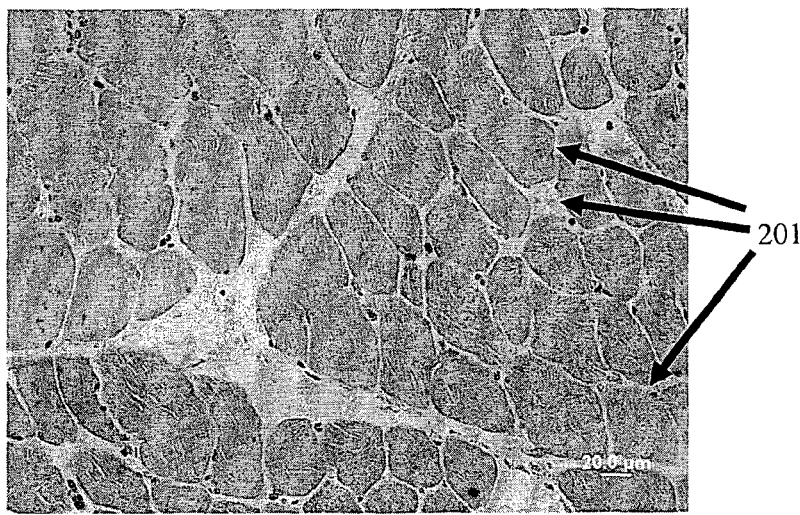
FIG. 2. Marbling damage in a section of tibialis anterior muscle which had been made ischaemic and subsequently reperfused.
Figure 3:
FIG. 3. Fibre waviness damage in a section of tibialis anterior muscle which had been made ischaemic and subsequently reperfused.
Figure 4:
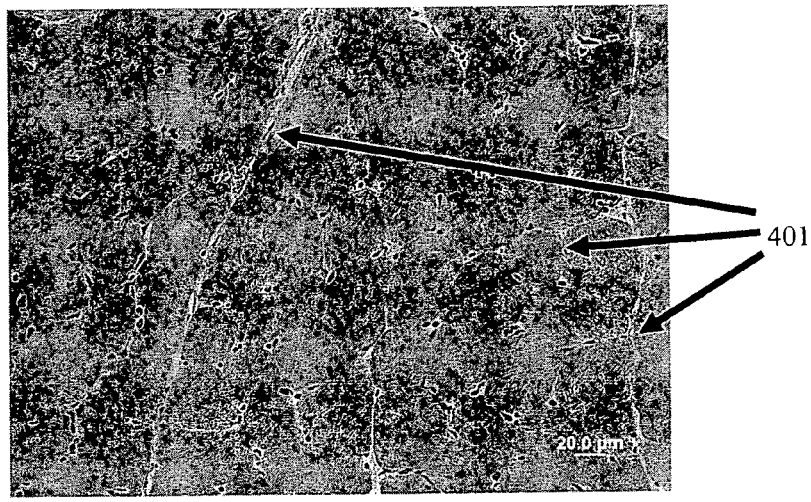
FIG. 4. A section of tibialis anterior muscle which had been pre-treated with riluzole prior to ischaemia.
Figure 5:
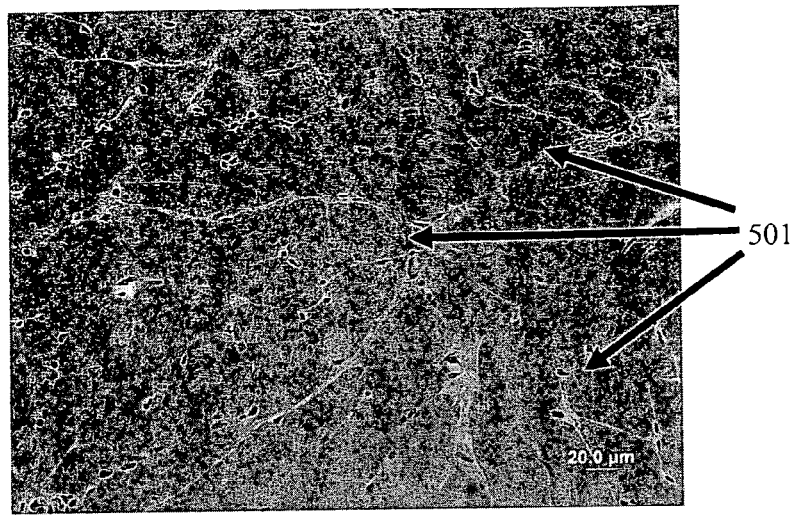
FIG. 5. A section of tibialis anterior muscle which had been pre-treated with riluzole prior to ischaemia and subsequent reperfusion.

Using H&E (hematoxylin and eosin) tissue staining, the tibialis anterior was studied in four groups of experimental animals: 1) with no damage and no treatment, 2) with ischaemia and reperfusion damage but no treatment, 3) with ischaemia damage and prior treatment with Riluzole, and 4) with ischaemia and reperfusion damage and prior treatment with Riluzole. In group 1) where there was no damage, there was minimal marbling of tissue as shown in FIG. 1. In group 2), there was extensive marbling of tissue indicative of extensive oedema as exemplified by the pale lines and regions such as those indicated at 201 in FIG. 2. Group 2) also showed extensive muscle waviness as exemplified by the waveshapes in the tissue fibres at 301 in FIG. 3. Oedema and fibre waviness are both associated with extensive tissue damage and thus FIGS. 2 and 3 demonstrate considerable damage by ischaemia and reperfusion when compared with the non-damaged tissue shown in FIG. 1. In group 3), there was slight marbling indicative of slight oedema as exemplified at 401 in FIG. 4, however this was considerably less than the extent of marbling in non-treated tissue as shown in FIG. 2. There was no tissue fibre waviness in Group 3). The minimal oedema and lack of waviness indicates that ischaemic damage was minimal when the tissue was pre-treated with Riluzole. Group 4), showed slightly more marbling than group 3) as exemplified at 501 in FIG. 5, but still very little marbling when compared with group 2) at 201 in FIG. 2. There was no tissue fibre waviness in group 4). Therefore, in this example, persistent sodium current blockade with Riluzole significantly reduced the extent of oedema in both ischaemic (at 401 in FIG. 4) and reperfused (at 501 in FIG. 5) tissue fibres when compared with non-treated tissue at 201 in FIG. 2. Riluzole also significantly reduced or possibly eliminated the extent of tissue fibre waviness in both ischaemic and reperfused tissue fibres when compared with non-treated tissue at shown at 301 in FIG. 3. Thus Riluzole significantly reduced the speed and/or extent of tissue damage caused by ischaemia or by reperfusion as assessed by H&E tissue-staining.

Example 2

Figure 6:
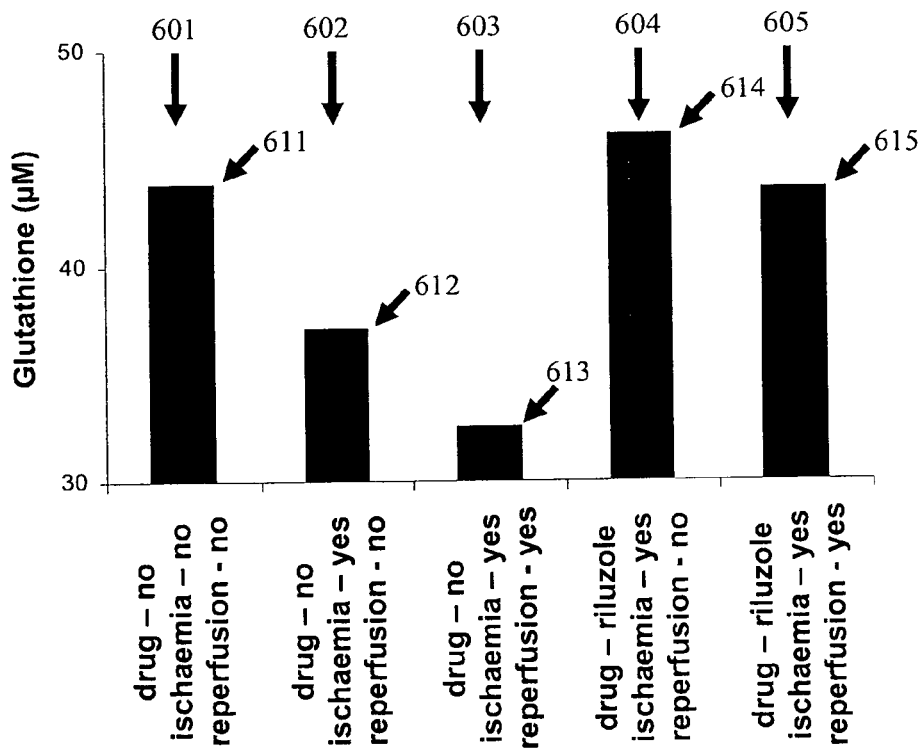
FIG. 6. A graph comparing average glutathione levels from several samples of tibialis anterior muscle which were either not exposed to riluzole or ischaemia or reperfusion, or were exposed to ischaemia with or without reperfusion and with or without riluzole.

Persistent sodium current blockade was also evaluated for its effect on tissue glutathione levels during ischaemia and reperfusion. FIG. 6 shows a graph of average glutathione levels in each of five groups of experimental animals—those with no drug, no ischaemia and no reperfusion as shown at 601, those with no drug, with ischaemia and with no reperfusion as shown at 602, those with no drug, with ischaemia and with reperfusion as shown at 603, those with riluzole, with ischaemia and no reperfusion as shown at 604, and those with riluzole, with ischaemia and with reperfusion as shown at 605. As shown at 612, ischaemia alone in non-treated tissue significantly reduced the level of glutathione when compared with no ischaemia and no treatment at 611. Moreover, as shown at 613, reperfusion in non-treated tissue significantly reduced the level of glutathione when compared with ischaemia alone in non-treated tissue at 612 and when compared with no ischaemia and no treatment at 611. These results demonstrate the detrimental effect of ischaemia and of reperfusion in non-treated tissue. However, as shown at 614, the level of glutathione in persistent sodium current blockaded tissue exposed to ischaemia but not reperfusion, was comparable with that in non-treated and non-ischaemic tissue as shown at 611. Furthermore, the level of glutathione in persistent sodium current blockaded tissue exposed to ischaemia as shown at 614 was significantly greater than that in non-treated ischaemic tissue as shown at 612. Similarly, as shown at 615, the level of glutathione in persistent sodium current blockaded tissue exposed to ischaemia and reperfusion, was comparable with that in non-treated and non-ischaemic tissue as shown at 611. Furthermore, the level of glutathione in persistent sodium current blockaded tissue exposed to ischaemia and reperfusion as shown at 615 was significantly greater than that in non-treated ischaemic and reperfused tissue as shown at 613. These latter results demonstrate that persistent sodium current blockade does overcome the detrimental effects of ischaemia and of reperfusion in non-treated tissue. Hence persistent sodium current blockade significantly reduced the speed and/or extent of muscle damage caused by ischaemia or by reperfusion as assessed by glutathione levels.

Example 3

Figure 7:
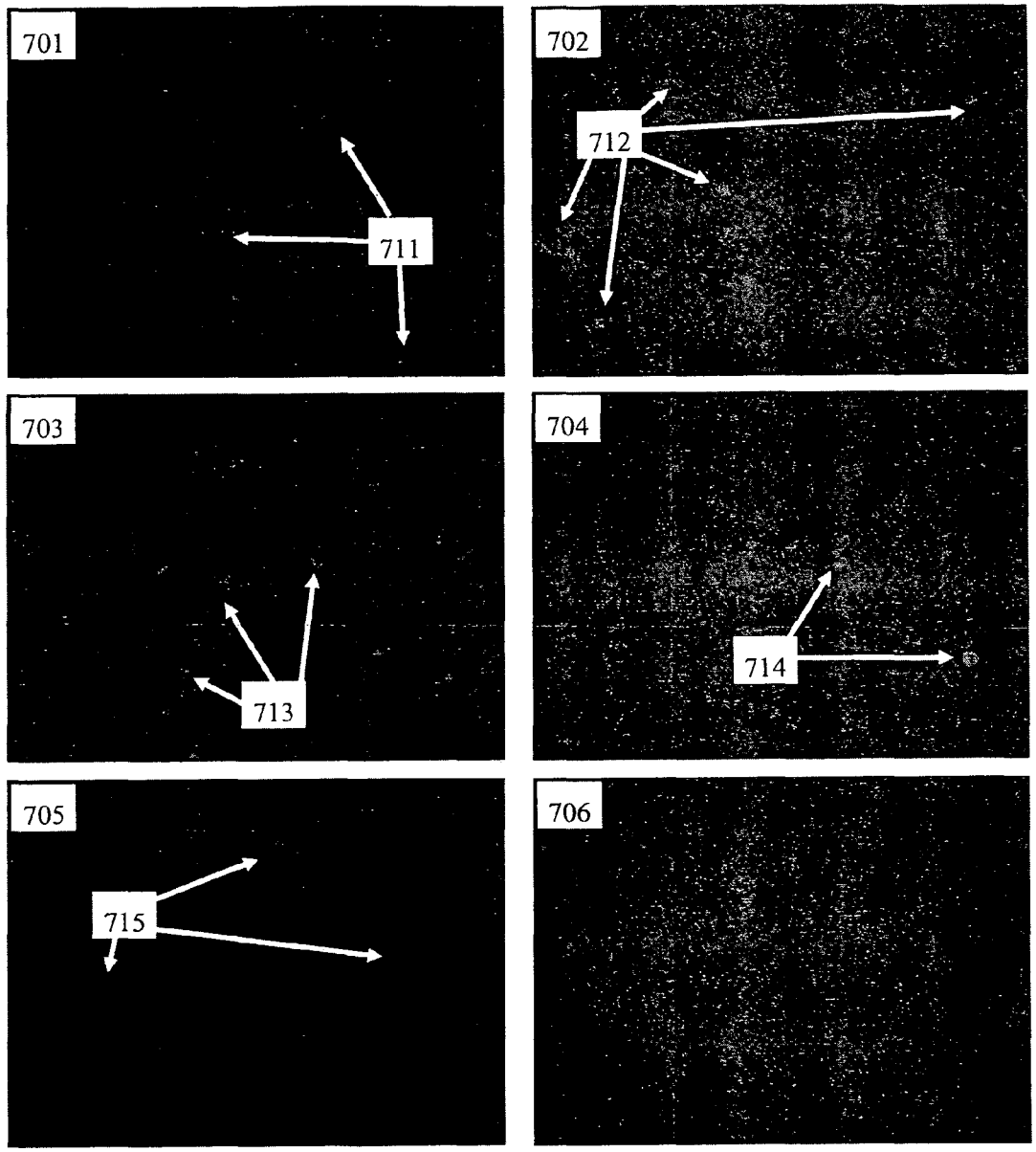
FIG. 7. DNA fragmentation in samples of tibialis anterior muscle exposed to ischaemia-reperfusion, riluzole prior to ischaemia, and riluzole prior to reperfusion.

In addition, persistent sodium current blockade was assessed for its affect on tissue DNA fragmentation during ischaemia and reperfusion. FIG. 7 shows 6 panels—701, 702, 703, 704, 705 and 706. Panels 701 and 702 are paired in that they show exactly the same section of tissue from the same animal. The difference between panels 701 and 702 is that they have been illuminated under different lighting conditions with panel 701 having been illuminated by light with wavelength greater than 620 nm, and panel 702 having been illuminated by light with wavelength around 520 nm. Similarly, panels 703 and 704 show the same section of tissue from the same animal with panel 703 having been illuminated by light with wavelength greater than 620 nm, and panel 704 having been illuminated by light with wavelength around 520 nm. In addition, panels 705 and 706 show the same section of tissue from the same animal with panel 705 having been illuminated by light with wavelength greater than 620 nm, and panel 706 having been illuminated by light with wavelength around 520 nm. The purpose of illuminating tissue under different frequency light is to see different structures. When illuminated with light with a wavelength greater than 620 nm, nuclei in the tissue fluoresce and become visible. When illuminated with light with a wavelength around 520 nm, damaged nuclei (DNA fragmentation) in the tissue fluoresce and become visible. The reason for using the two different wavelengths is to enable a comparison of position between fluorescing regions so that one doesn't mistake a region fluorescing under 520 nm light as being damaged nuclei when there are not any nuclei in that region.

In FIG. 7, the tissue in panel-pair 701 and 702 was exposed to ischaemia and reperfusion but was not treated with persistent sodium current blockade. As can be seen at 711 in panel 701, there are many nuclei in the tissue sample—these are seen as pale non-spherical dots. Only three of the many regions of nuclei are indicated by arrows 711. In pair-panel 702, there are also many pale non-spherical dots—these are damaged nuclei and five of these are shown at 712. Thus panel 701 shows a section of tissue with many nuclei and panel 702 shows in the same section of tissue many nuclei which have been damaged by ischaemia and reperfusion.

The tissue in panel-pair 703 and 704 was treated with persistent sodium current blockade prior to being made ischaemic. This tissue was not reperfused. As with panel 701, panel 703 shows many nuclei in the sample, three of which are pointed to at 713. However, unlike panel 702, panel 704 does not show any damaged nuclei. While there are two spherical dots at 714, these do not align with the nuclei shown in panel 702 and are thus not damaged nuclei. Most likely, they are blood vessels. Therefore, panel-pair 703 and 704 show that ischaemia did not damage nuclei pre-treated with persistent sodium current blockade.

The tissue in panel-pair 705 and 706 was treated with persistent sodium current blockade prior to being made ischaemic and being reperfused. As with panels 701 and 703, panel 705 shows many nuclei in the sample, three of which are pointed to at 715. However, in similarity to panel 704, panel 706 does not show any damaged nuclei. Therefore, panel-pair 705 and 706 show that ischaemia and reperfusion did not damage nuclei pre-treated with persistent sodium current blockade. More-over, by comparing panel-pair 703 and 704 with panel-pair 705 and 706, panel-pair 705 and 706 show that reperfusion did not damage nuclei pre-treated with persistent sodium current blockade.

FIG. 7 demonstrates that persistent sodium current blockade significantly reduced the speed and/or extent of tissue damage caused by ischaemia or by reperfusion as assessed by DNA fragmentation.

Studies on Kidney Tissue of Wistar Albino Rats

Additional studies were performed on kidney tissue in 48 isoflurane-anaesthetised, male Wistar albino rats (300-350 g). In all animals, riluzole at 5 mg/kg (n=12), lidocaine at 1 mg/kg (n=12), lamotrigine at 20 mg/kg (n=12) or saline (n=12, non-treated group) was infused intravenously over ten minutes. A further ten minutes was allowed for drug circulation prior to the induction of ischaemia. Tissue ischaemia was produced in all animals by occluding the renal artery to the left kidney. Immediately prior to occlusion, a 1,000 unit bolus of IV heparin was injected to prevent blood clotting and to permit reperfusion. Occlusion was maintained for 3 hours following which, in 6 animals in each group, the occlusion was released and reperfusion of the kidney was allowed. Samples of reperfused tissue were excised 45 minutes following reperfusion. Samples of non-reperfused ischaemic tissue were excised 3 hours post occlusion. Samples of ischaemic tissue and of reperfused tissue were taken from different animals. Samples of non-ischaemic, non-treated tissue were excised from the right kidney of the non-treated group.

Example 4

Figure 8:
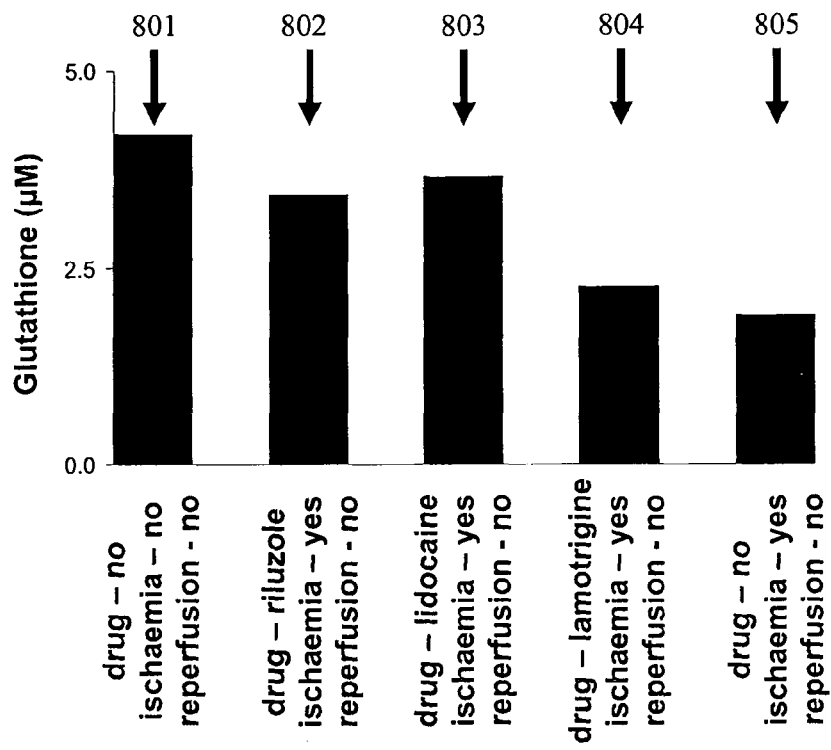
FIG. 8. A graph comparing average glutathione levels from several samples of kidney tissue in isoflurane-anaesthetised male Wistar albino rats which were either not exposed to ischaemia, or were treated with riluzole, lidocaine, lamotrigine or no drug prior to induction of ischaemia.
Figure 9:
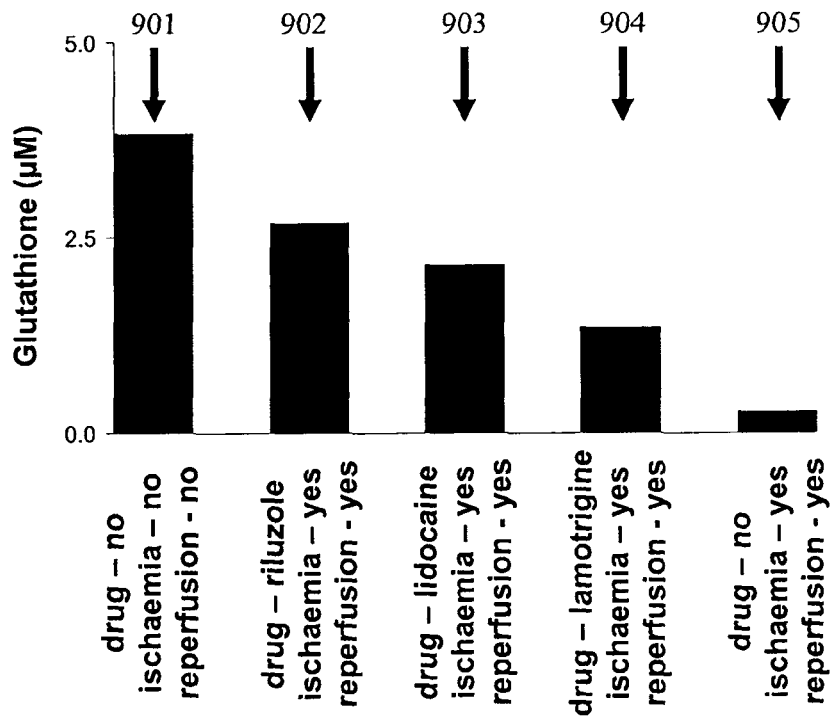
FIG. 9. A graph comparing average glutathione levels from several samples of kidney tissue in isoflurane-anaesthetised male Wistar albino rats which were either not exposed to ischaemia or reperfusion, or were treated with riluzole, lidocaine, lamotrigine or no drug prior to induction of ischaemia followed by reperfusion.

Persistent sodium current blockade was evaluated for its effect on kidney tissue glutathione levels during ischaemia and reperfusion. FIG. 8 shows a graph of average glutathione levels in each of five groups of non-reperfused experimental animals—those with no drug and no ischaemia as shown at 801, those with riluzole and ischaemia as shown at 802, those with lidocaine and ischaemia as shown at 803, those with lamotrigine and ischaemia as shown at 804, and those with no drug but with ischaemia as shown at 805. As shown at 805, ischaemia alone in non-treated tissue significantly reduced the level of glutathione when compared with no ischaemia and no treatment at 801. Conversely, glutathione levels in the riluzole at 802 and lidocaine at 803 groups were not significantly reduced by ischaemia. Indeed, the glutathione levels in the riluzole group at 802 and the lidocaine group at 803 were only marginally and not significantly reduced as compared with the non-treated and non-ischaemic group at 801. While glutathione levels in the lamotrigine ischaemic group at 804 were similar to the non-treated ischaemic group at 805, the glutathione levels in the lamotrigine reperfused group at 904 in FIG. 9 remained substantially higher than the non-treated reperfused group at 905. Moreover, the glutathione levels in the lidocaine reperfused group at 903 and in particular the glutathione levels in the riluzole reperfused group at 902 were significantly higher than in the non-treated reperfused group at 905 and more similar, and not significantly different from, the non-treated, non-ischaemic and non-reperfused group shown at 901. As expected, the glutathione levels in the non-treated, ischaemic and reperfused group shown at 905 were far more compromised than the non-treated ischaemic but not reperfused group shown at 805 in FIG. 8 demonstrating the damaging effects of reperfusion. These results demonstrate the detrimental effect of ischaemia and of reperfusion in non-treated tissue. More-over, these results demonstrate that persistent sodium current blockade significantly overcomes the detrimental effects of ischaemia and of reperfusion in non-treated tissue. While these results show that some compounds are more effective than others at reducing the effects of ischaemia and of reperfusion on the kidney, persistent sodium current blockade was shown to reduce the extent of kidney damage caused by ischaemia or by reperfusion as assessed by glutathione levels.

Example 5

Figure 10:
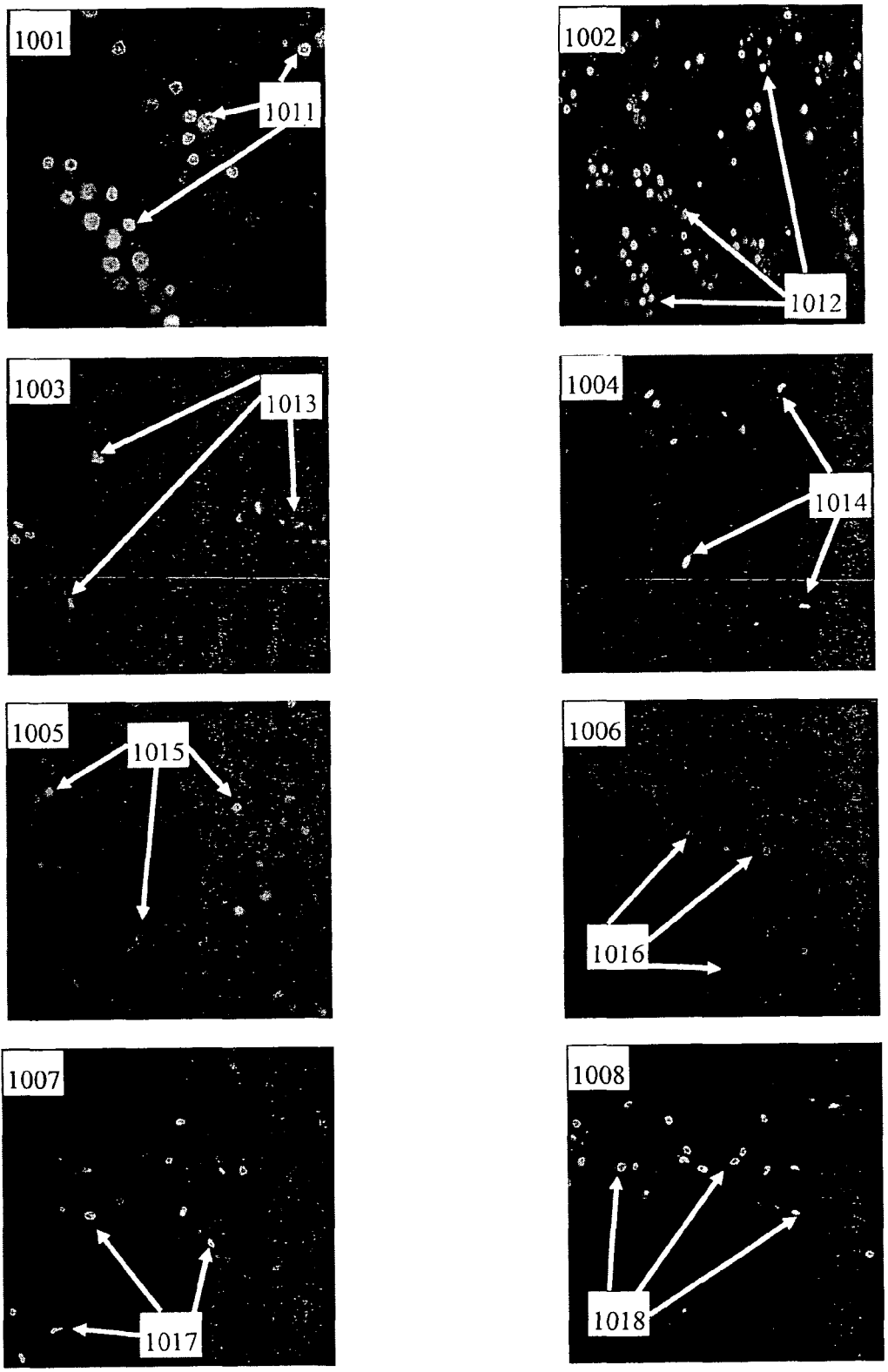
FIG. 10. DNA fragmentation in samples of kidney tissue in isoflurane-anaesthetised male Wistar albino rats following ischaemia with or without reperfusion, wherein the tissue samples were not treated or were treated with either riluzole, lidocaine or lamotrigine.

In addition, persistent sodium current blockade was assessed for its affect on kidney tissue DNA fragmentation during ischaemia and reperfusion. FIG. 10 shows 8 panels of DNA fragmentation in sections of renal tubules at ×60 magnification following 3 hours of ischaemia and no reperfusion (left-hand panels 1001, 1003, 1005 and 1007), and following 3 hours of ischaemia and 45 minutes of reperfusion (right-hand panels 1002, 1004, 1006 and 1008). All panels were illuminated by light with wavelength around 520 nm to show DNA fragmentation. Panels 1001 and 1002 show DNA fragmentation in non-treated tissue; panels 1003 and 1004 show DNA fragmentation in riluzole-treated tissue; panels 1005 and 1006 show DNA fragmentation in lidocaine-treated tissue; and panels 1007 and 1008 show DNA fragmentation in lamotrigine-treated tissue.

As can be seen in panel 1001, and as exemplified by 1011, many nuclei were damaged by the 3-hour period of ischaemia. As expected, panel 1002 shows an even greater number of nuclei damaged by 3 hours of ischaemia followed by 45 minutes of reperfusion as exemplified at 1012. In comparison, however, panel 1003 shows considerably fewer damaged nuclei in the riluzole-treated ischaemic group and panel 1004 similarly shows relatively few damaged nuclei in the riluzole-treated ischaemia-reperfusion group (as exemplified at 1013 and 1014 respectively). Although not quite as effective as the riluzole-treated groups, the lidocaine-treated ischaemic and ischaemia-reperfusion groups shown in panels 1005 and 1006 respectively show considerably fewer damaged nuclei than in the non-treated groups (panels 1001 and 1002 respectively). The lamotrigine-treated ischaemic tissue (panel 1007) and ischaemia-reperfusion tissue (panel 1008) showed that lamotrigine is not as effective as riluzole (panels 1003 and 1004 respectively), however, the reduction in damaged nuclei is still significant over the non-treated tissue (panels 1001 and 1002 respectively).

FIG. 10 demonstrates that persistent sodium current blockade significantly reduced the extent of tissue damage caused by ischaemia or by reperfusion as assessed by DNA fragmentation.

We claim:

1. A method for the treatment or amelioration of non-neuronal and non-myocardial cell or tissue damage or death, comprising administering to a mammal in need thereof a therapeutically effective amount of a persistent sodium current blocker or a pharmaceutically acceptable salt thereof;
   wherein the non-neuronal and non-myocardial cell or tissue damage or death occurs in skeletal muscle tissue, smooth muscle tissue, connective tissue or epithelial tissue; and
   wherein the persistent sodium current blocker is selected from the group consisting of lidocaine, mexiletine, lamotrigine, BW1003C87 ([5-(2,3,5-trichlorophenyl)pyrimidine-2,4-diamine 1.1 ethanesulphonate]), sipatrigine, phenytoin, fosphetrytoin, riluzole, flunarizine, CP-060S ((−)-(S)-2-[3,5-bis(1,1-dimethylethyl)-4-hydroxyphenyl]-3-[3-[N-methyl-N-[2-(3,4-methylenedioxy-phenoxy)ethyl]amino]propyl]-1,3-thiazolidin-4-one hydrogen fumarate), R56865 (N-[1-(4-(4-fluorophenoxy)butyl)]-4-piperidinyl-N-methyl-2-benzo-thiazolamine), flecainide, azure A, and F15845 (3-(R)-[3-(2-methoxyphenylthio-2-(S)-methyl-propyl]amino-3,4-dihydro-2H-1,5-benzoxathiepine bromohydrate) or a pharmaceutically acceptable salt thereof.

2. The method according to claim 1, wherein the non-neuronal and non-myocardial cell or tissue damage or death arises from any one of hypoxia, ischaemia, reperfusion, ischaemia-reperfusion injury, infarction, necrosis, free tissue transfer, organ transplant, disease, hypertrophy, inflammation, scarring, physical injuries, crush injuries, lacerations, tourniquet, medical interventions, surgical interventions or procedures, exposure to chemicals, toxins, bacteria, viruses or radiation, tissue reperfusion or other form of alteration to the normal function of the cells, tissues or organs.

3. The method according to claim 1, wherein the non-neuronal and non-myocardial cell or tissue damage or death arises from hypoxia, ischaemia, reperfusion or ischaemia-reperfusion injury.

4. The method according to claim 1, wherein the non-neuronal and non-myocardial cell or tissue damage or death arises from physical injuries, crush injuries, lacerations medical interventions, or surgical interventions or procedures.

5. The method according to claim 1, wherein the speed of development of non-neuronal and non-myocardial cell or tissue damage or death is reduced, or the speed of degradation of non-neuronal and non-myocardial cell or tissue damage is reduced, or the speed of recovery of non-neuronal and non-myocardial cell or tissue damage is enhanced.

6. The method according to claim 1, wherein the non-neuronal and non-myocardial cell or tissue damage or death is associated with free tissue transfer or tissue transplant.

7. The method according to claim 6, wherein the tissue to be transferred or transplanted is treated prior to or during or post transfer or transplant with a therapeutically effective amount of the persistent sodium current blocker or a pharmaceutically acceptable salt thereof.

8. The method according to claim 1, wherein the non-neuronal and non-myocardial cell or tissue damage or death is due to a loss or reduction in blood or oxygen supply.

9. The method according to claim 1, wherein the pain associated with the non-neuronal and non-myocardial cell or tissue damage or death is reduced.

10. The method according to claim 1, wherein the persistent sodium current blocker is selected from the group consisting of riluzole, lidocaine and lamotrigine or a pharmaceutically acceptable salt thereof.

11. The method according to claim 10, wherein the persistent sodium current blocker is riluzole or a pharmaceutically acceptable salt thereof.

12. The method according to claim 1, wherein the mammal is human.

13. The method according to claim 7, wherein the tissue to be transferred or tissue to be transplanted is selected from the group consisting of skeletal muscle tissue, smooth muscle tissue, connective tissue, epithelial tissue, skin, subcutaneous tissue, fat and adipose tissue, bone, blood vessels, lymphatic vessels and reproductive tissue including germ cells.

14. The method according to claim 7, wherein the persistent sodium current blocker is selected from the group consisting of riluzole, lidocaine and lamotrigine or a pharmaceutically acceptable salt thereof.

15. The method according to claim 14, wherein the persistent sodium current blocker is riluzole or a pharmaceutically acceptable salt thereof.

16. The method according to claim 6, wherein the mammal is human.

17. The method according to claim 3, wherein the mammal is human and wherein the persistent sodium current blocker is selected from the group consisting of riluzole, lidocaine and lamotrigine or a pharmaceutically acceptable salt thereof.

18. The method according to claim 17, wherein the persistent sodium current blocker is riluzole or a pharmaceutically acceptable salt thereof.

19. The method according to claim 4, wherein the mammal is human and wherein the persistent sodium current blocker is selected from the group consisting of riluzole, lidocaine and lamotrigine or a pharmaceutically acceptable salt thereof.

20. The method according to claim 19, wherein the persistent sodium current blocker is riluzole or a pharmaceutically acceptable salt thereof.

* * * * *